United States Patent [19]

Stevens et al.

[11] Patent Number: 5,599,577

[45] Date of Patent: Feb. 4, 1997

[54] SIMETHICONE CONTAINING PHARMACEUTICAL COMPOSITIONS

[75] Inventors: Charles A. Stevens, Lansdale; Michael R. Hoy, North Wales; Edward J. Roche, Paoli, all of Pa.

[73] Assignee: McNeil-PPC, Inc., Skillman, N.J.

[21] Appl. No.: 455,427

[22] Filed: May 31, 1995

Related U.S. Application Data

[60] Division of Ser. No. 38,397, Mar. 29, 1993, abandoned, which is a continuation-in-part of Ser. No. 887,207, May 21, 1992, abandoned.

[51] Int. Cl.$^6$ .............................. B05D 3/12; A61K 9/24; A61J 3/00
[52] U.S. Cl. ..................... 427/2.14; 424/472; 514/960
[58] Field of Search ........................ 427/2.14, 2.21; 424/472; 264/135; 514/690

[56] References Cited

U.S. PATENT DOCUMENTS

| | | | |
|---|---|---|---|
| 3,048,526 | 8/1962 | Boswell | 424/472 |
| 3,767,794 | 11/1969 | McVean et al. | 424/21 |
| 4,127,650 | 3/1975 | Buchler | 424/184 |
| 4,198,390 | 4/1980 | Rider | 424/21 |
| 4,316,888 | 4/1980 | Nelson | 424/127 |
| 4,396,604 | 8/1983 | Mitra | 424/154 |
| 4,857,324 | 8/1989 | Mir et al. | 424/69 |
| 5,075,114 | 12/1991 | Roche | 424/470 |
| 5,116,847 | 5/1992 | Gilbert et al. | 514/327 |
| 5,248,505 | 9/1993 | Garwin | 424/472 |
| 5,275,819 | 1/1994 | Amer et al. | 424/408 |
| 5,288,507 | 2/1994 | Sims | 424/682 |
| 5,417,980 | 5/1995 | Goldman et al. | 424/464 |
| 5,447,918 | 9/1995 | McCullough | 514/53 |

FOREIGN PATENT DOCUMENTS

| | | |
|---|---|---|
| 1042796 | 11/1978 | Canada. |
| 1139221 | 1/1983 | Canada. |
| 0428296 | 5/1991 | European Pat. Off.. |
| 0439315A1 | 7/1991 | European Pat. Off.. |
| 1038M | of 1962 | France. |
| 2557429 | 7/1985 | France. |

OTHER PUBLICATIONS

J. Alfred Rider, "An Improved Simethicone Antacid Tablet", pp. 1033–1038 (1981) no month.
F. Maksoud, S. A. Said and M. Gourab, "Simethicone Use in Antacid Medications", pp. 35 and 36 (1976) no month.
J. K. Lalla and M. A. Sarkar, "Preparation and Stability Testing of Simethicone Emulsion", pp. 159–166 (1985) no month.
Cellulose Esters Polymer Characterization, Bulletin CE–2, FMC Corp. (1987) no month.
Cellulose Esters Polymers for Novel Drug Delivery, Bulletin CE–1, FMC Corp. (1986) no month.
CA115(24):263465f, Pharmaceutical Composition for Treating Gastrointestinal Distress (1991) no month.
CA111(2):12462a, Incorporation of Simethicone into Syrupy or Clear Base Liquid Orals (1989) no month.
CA97(13): 103890x, The Effect of Activated Dimethicone and an Proprietary Antacid Preparation Containing this Agent on the Absorption of Phenytoin (1982) no month.

(List continued on next page.)

*Primary Examiner*—Diana Dudash
*Attorney, Agent, or Firm*—Bernard F. Plantz

[57] ABSTRACT

A method of making solid oral dosage form for the treatment of gastrointestinal disorders comprising a therapeutically effective amount of a pharmaceutical suitable for the treatment of gastric disorders selected from the group consisting of cimetidine, ranitidine, famotidine, diphenoxylate, loperamide, loperamide-N-oxide, pharmaceutically acceptable salts thereof and combinations thereof; and a therapeutically effective amount of simethicone wherein the pharmaceutical and simethicone are separated by a barrier. The barrier is formed by coating with a polymer impermeable to simethicone.

5 Claims, 5 Drawing Sheets

OTHER PUBLICATIONS

CA96(25):210465p, The Effect of Activated Dimethicone, Other Antacid Constituents, and Kaolin on the Absorption of Propranolol (1982) no month.

CA93(14):138018p, Uniform Beadlike Particles Forming a Powder Surpuriya (1980) no month.

CA90(17):132533u, Interaction of Digoxin with Activated Dimethicone and Other Antacid Constituents (1979) no month.

CA107(4):28386g, Drugs in Combined Gastro–Soluble and Gastro–Resistant Form (1986) no month.

C71–S36634, Flatulence Treatment with Antifoaming–Compn (1974) no month.

C75–W80496, Medicaments for Treating Nervous Hyperacidity, Etc.–Contg. a Psychosedative, an Antacid, and an Antiflatuent (1975) no month.

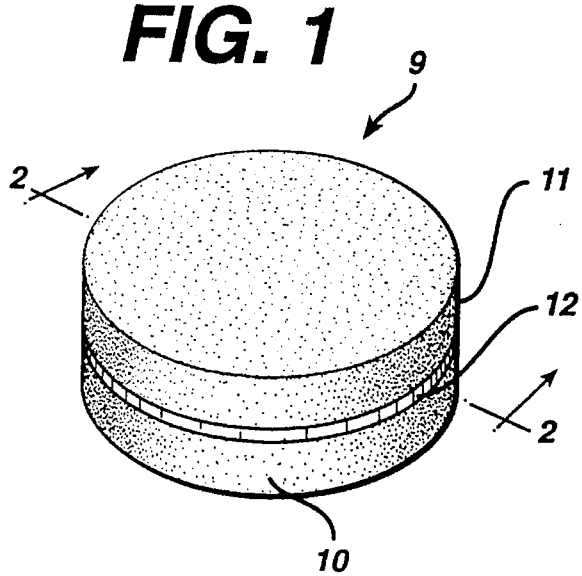
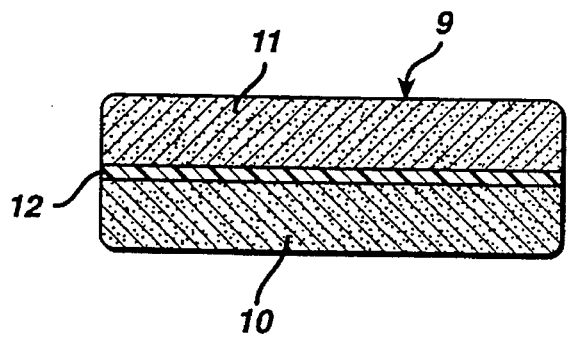
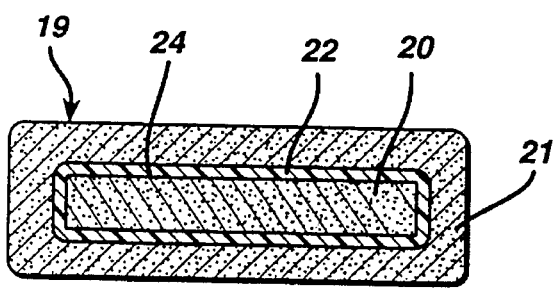
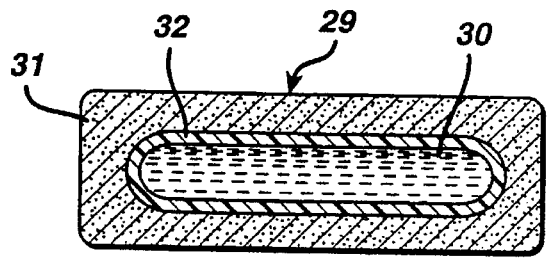

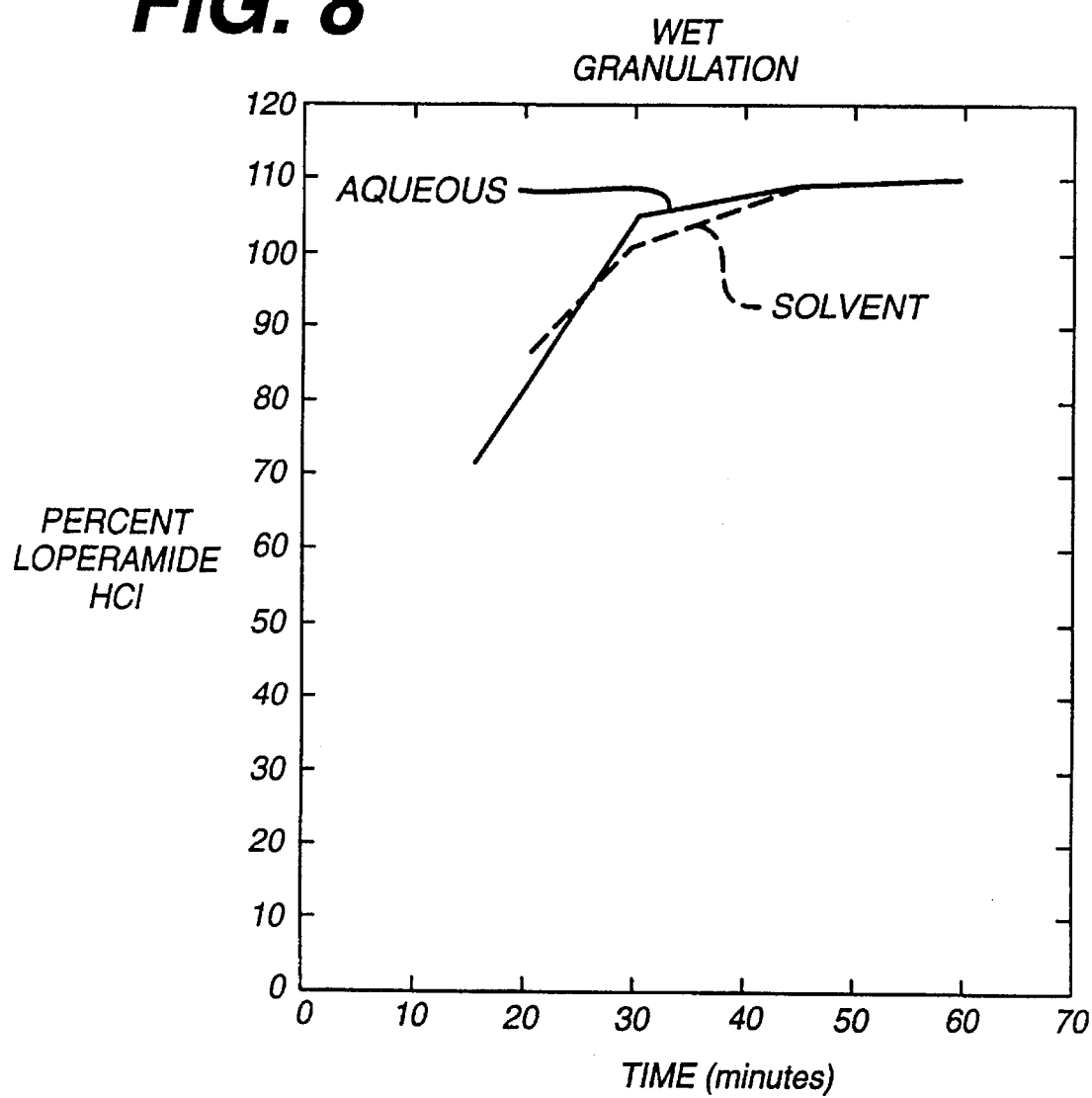

5,599,577

1

SIMETHICONE CONTAINING PHARMACEUTICAL COMPOSITIONS

This is a division of application Ser. No. 08/038,397, filed Mar. 29, 1993, now abandoned which is a continuation-in-part of application Ser. No. 07/887,207, filed May 21, 1992, abandoned, all of which are hereby incorporated by reference.

FIELD OF INVENTION

This invention relates to a solid oral dosage form for a pharmaceutical composition for treating gastrointestinal distress comprising a therapeutically effective amount of simethicone and a therapeutically effective amount of an antidiarrheal, an antiperistaltic and/or an $H_2$ blocker. This invention also relates to methods of making the aforesaid solid oral dosage form.

BACKGROUND OF THE INVENTION

Simethicone has been utilized in a variety of therapeutic liquid and solid dosage forms. The most common dosage formulations for simethicone are combinations of simethicone with various separate antacids. In this dosage formulation it is necessary to separate the simethicone from the antacid to avoid the inactivation of the simethicone. Other formulations of simethicone have been suggested in the literature such as simethicone and dextromethorphan, and simethicone, tranquilizer and an antacid.

Simethicone may advantageously be combined with an antidiarrheal or antiperistaltic to provide enhanced relief for gastrointestinal distress due to diarrhea.

However, in formulating simethicone with these antidiarrheals, antiperistaltics and $H_2$ blockers, we discovered that without special precautions being taken, the dissolution rate of the antidiarrheals, antiperistaltics and $H_2$ blockers was adversely effected.

SUMMARY OF THE INVENTION

In accordance with the present invention, we have discovered a solid oral dosage form for the treatment of gastrointestinal disorders comprising a therapeutically effective amount of a pharmaceutical suitable for the treatment of gastric disorders selected from the group consisting of cimetidine, ranitidine, famotidine, diphenoxylate, loperamide, loperamide-N-oxide, pharmaceutically acceptable salts thereof and combinations thereof; and a therapeutically effective amount of simethicone wherein the oral dosage form has a first portion containing the simethicone and a second portion containing the pharmaceutical suitable for the treatment of gastric disorders wherein the first and second portions are in contact with and separated by a barrier which is substantially impermeable to simethicone.

In an another embodiment of the present invention, we have further discovered a solid oral dosage form for the treatment of gastrointestinal disorders comprising a therapeutically effective amount of a pharmaceutical suitable for the treatment of gastric disorders selected from the group consisting of cimetidine, ranitidine, famotidine, diphenoxylate, loperamide, loperamide-N-oxide, pharmaceutically acceptable salts thereof and combinations thereof wherein the pharmaceutical suitable for the treatment of gastric disorders is provided in the form of coated granules which are coated with a nonenteric coating impermeable to simethicone; a therapeutically effective amount of simethicone; and pharmaceutically acceptable excipients.

In a further embodiment of the invention we have discovered a method for manufacturing the multilayered solid dosage form having one layer containing simethicone and one layer containing a pharmaceutical suitable for treating gastric disorders with a barrier sandwiched between the two layers comprising pressing one of two granulations, each containing pharmaceutically acceptable excipients with either a therapeutic amount of simethicone or a therapeutic amount of a pharmaceutical suitable for the treatment of a gastric disorder therein, to form a first layer with one exposed surface; then coating the exposed surface with a material which is substantially impermeable to simethicone to form a coated layer with a coated surface; contacting the coated surface with the remaining granulation; then pressing the granulation and coated layer to form a multilayered solid oral dosage form wherein the simethicone and the pharmaceutical are separated by the material substantially impermeable to simethicone.

Other aspects, objects and several advantages of this invention will be apparent from the foregoing specification and claims.

BRIEF DESCRIPTION OF THE DRAWINGS

FIG. 1 is a perspective view of a pharmaceutical tablet in accordance with one embodiment of the present invention;

FIG. 2 is a sectional view of an embodiment of the present invention;

FIG. 3 is a sectional view of another embodiment of the present invention; and

FIG. 4 is a sectional view of a third embodiment of the present invention.

FIG. 8 provides dissolution profiles for tablets that contain coated loperamide HCl granules admixed with granules of simethicone. The solid line indicates the dissolution profile for the tablet prepared with an aqueous granulating liquid. The dashed line indicates the dissolution profile for the tablet prepared with a solvent (water/propanol) granulating liquid. The formulations for these tablets are contained in Example III.

DETAILED DESCRIPTION

Figure 5:
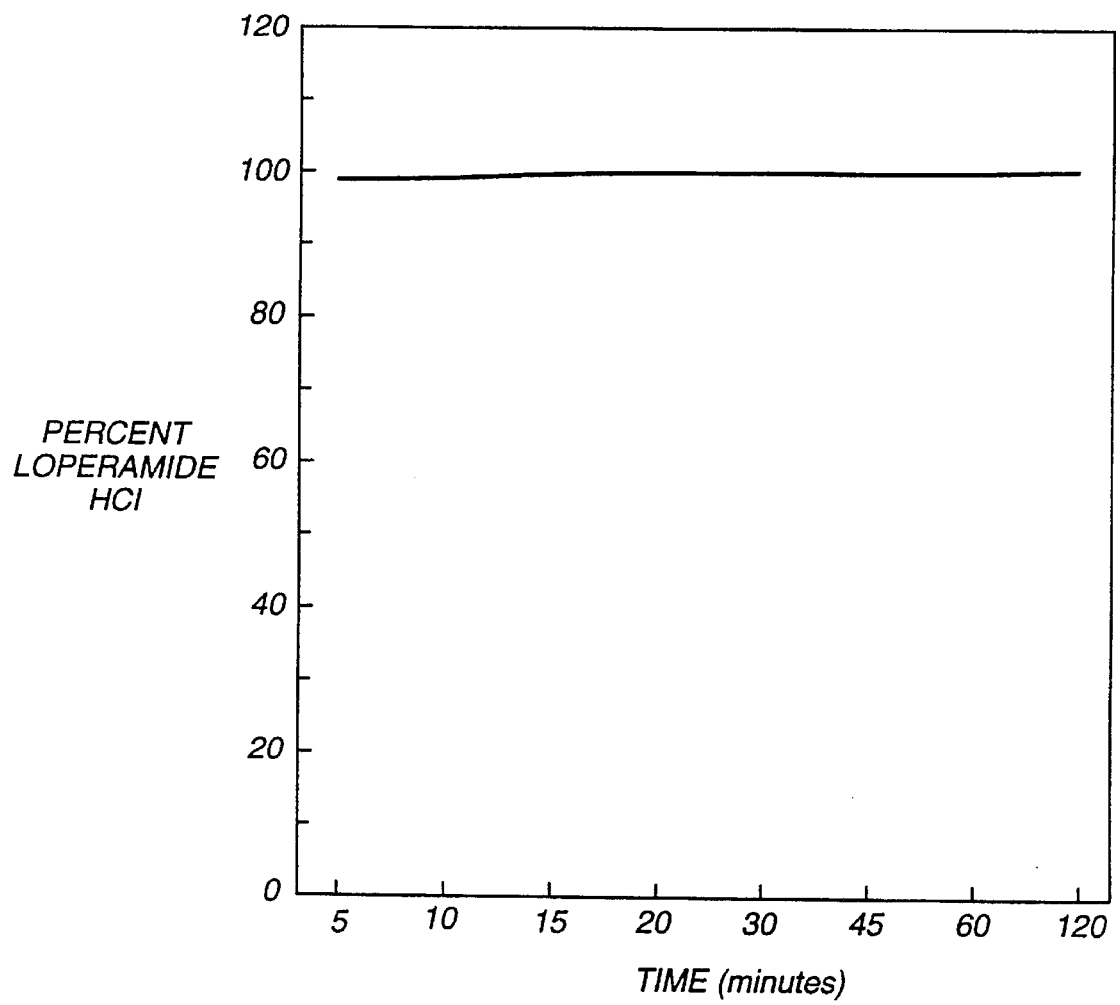
FIG. 5 provides a dissolution profile for uncoated loperamide present with simethicone provided in separate solid oral dosage forms. All the dissolution profiles hereinafter were performed in accordance with the procedure set forth in the U.S. Pharmacopeia XXII as modified in Supplement 1. The solid dosage form of loperamide was provided by an Imodium AD brand antidiarrheal tablet. The simethicone for this test was provided by a Mylicon brand antiflatulent tablet.

Referring to FIGS. 1 and 2, indicated generally as 9 is a tablet constructed in accordance with one of the embodiments of the invention. Tablet 9 comprises a first portion or layer 10 containing simethicone and a second portion or layer 11 containing a pharmaceutical suitable for the treatment of gastric disorders with each of the first and second layers 10, and 11 being separate and discrete from the other layer. Sandwiched between layers 10 and 11 is a barrier 12 which may be a film or diaphragm or membrane composed of plastic material. Barrier 12 maintains the simethicone in first layer 10 out of contact with the pharmaceutical suitable for the treatment of gastric disorders in second layer 11 and prevents migration of the simethicone from layer 10 to layer 11 as well as preventing migration of the pharmaceutical for the treatment of gastric disorders from layer 11 to layer 10.

Referring to FIG. 3, in this embodiment 19, the first portion containing the simethicone is in the form of an inner core 20, and the second portion comprising the pharmaceutical suitable for the treatment of gastric disorders is in the form of an outer layer 21 encompassing inner core 20. Barrier 22 is disposed between inner core 20 and outer layer 21 and encompasses inner core 20. Outer layer 21 encompasses barrier 22. Barrier 22 may be in the form of a thin plastic film or sheet surrounding and enclosing inner core 20, or barrier 22 may be in the form of a thin plastic film applied as a coating on the outer surface 24 of inner core 20 before outer layer 21 is formed.

In the embodiments of FIGS. 2 and 3, the portions 10 and 20, containing the simethicone, are each a mixture of ingredients comprising simethicone and a solid, inert filler or carrier or other simethicone adsorbing material.

Referring to FIG. 4, in this embodiment 29, the first portion comprising the simethicone is in the form of an inner core 30 which may consist entirely of simethicone in its natural, viscous liquid condition. The outer core comprising the pharmaceutical suitable for the treatment of gastric disorders 31 may be similar to the outer core 21 in the embodiment of FIG. 3. The inner core of simethicone is encompassed by and contained within a barrier 32 which may be in the form of a container for the liquid simethicone, e.g. a soft, chewable gelatin capsule shell. As an alternative to providing the simethicone within container 21 in its natural, viscous liquid condition, the simethicone may be provided as part of a solid mixture, as is the case with both the simethicone-containing layer 10 in the embodiment 9 of FIG. 2 and the simethicone-containing inner core 20 in the embodiment 10 of FIG. 3.

In all of the above-described embodiments, the simethicone is separate from the matrix formed by the pharmaceutical suitable for the treatment of gastric disorders in its respective portion (11, 21 or 31), and the simethicone remains substantially separated from the matrix during an extended shelf life because the barrier (12, 22, 32) prevents the simethicone from migrating into the pharmaceutical suitable for the treatment of gastric disorders. The simethicone will be considered substantially separate from the pharmaceutical if the barrier prevents the simethicone from lowering the dissolution rate of the pharmaceutical more than 10% compared to the dissolution rate of an identically formulated solid dosage form not containing simethicone for at least 3 months at ambient temperature and humidity. Preferably the dissolution rate will not be affected for at least 6 months.

The barrier 12 or 22 is a pharmaceutically acceptable material and may be composed of a pharmaceutically acceptable film forming polymer which is physiologically inert and prevents the therapeutic ingredients in the separate portions of the solid dosage form from contacting. Suitable pharmaceutically acceptable polymers may be selected from the group consisting of cellulose derivatives, polyvinyl pyrrolidone, polyvinyl alcohol, polyvinyl acetate, polyethylene glycols, copolymers of styrene and acrylate, copolymers of acrylic acid and methacrylic acid, copolymers of methacrylic acid and ethylacrylate, copolymers of methyl methacrylate and methacrylate, copolymers of acrylic acid and tertiary amino alkyl methacrylate, copolymers of methacrylate and tertiary amino alkyl methacrylate, copolymers of ethylacrylate methyl methacrylate and quaternary amino alkyl methacrylate and combinations of two or more thereof. Cellulose derivatives includes pharmaceutically acceptable cellulose derivatives selected from the group consisting of methyl cellulose, hydroxypropyl methylcellulose, ethyl cellulose, hydroxyethyl cellulose, hydroxypropyl cellulose, carboxymethyl cellulose, cellulose acetate butyrate, cellulose acetate phthalate, hydroxypropyl methylcellulose phthalate, hydroxypropyl methylcellulose acetate succinate and combinations of two or more thereof. The acrylic acid and methacrylic acid copolymers listed above also includes copolymers of sodium and potassium salt thereof. A suitable ester copolymer of methacrylic and tertiary amino alkyl methacrylate is dimethylaminoethyl methacrylate-methacrylate. A suitable copolymer of ethylacrylate methyl methacrylate and quaternary amino alkyl methacrylate is (ethylacrylate-methyl methylacrylate) triethylaminoethyl methacrylate chloride.

The simethicone used in the present invention can be Simethicone USP or a commercially prepared granulation such as Simethicone GS (30% Simethicone USP adsorbed onto maltodextrins available from Union Carbide) or Simethicone GS-J (40% Simethicone USP adsorbed onto maltodextrins available from Union Carbide). The amount of simethicone contained in the solid dosage form should be sufficient to provide a therapeutic dosage to a patient suffering from gas or diarrhea and its associated symptoms. The preferred dosage ranges for simethicone is in the range of about 20 mg to about 125 mg per dosage unit, generally not to exceed 500 mg/day. The dosage ranges may vary for age and weight of a patient as well as the severity of symptoms.

The phrase "pharmaceutical suitable for the treatment of gastrointestinal disorders" is descriptive of a group of pharmaceuticals which have been found to be suitable for treating gastrointestinal disorders including but not limited to ulcers and diarrhea. Suitable pharmaceuticals for treating gastric disorders include pharmaceuticals selected from the group selected consisting of cimetidine, ranitidine, famotidine, diphenoxylate, loperamide, loperamide-N-oxide, pharmaceutically acceptable salts thereof and combinations thereof. A subset of this group of pharmaceuticals are chemically related compounds which appear to act by effecting the peristaltic activity of the circular and longitudinal muscles of the intestinal wall. This subset contains antidiarrheal or antiperistaltic compounds which include compounds selected from the group consisting of diphencoylate, loperamide, loperamide-N-oxide, pharmaceutically acceptable salts thereof, and combinations thereof. The phrase "combinations thereof" means the use of two or more of the enumerated pharmaceuticals for the treatment of a gastric disorder.

The amount of pharmaceutical suitable for the treatment of gastric disorder combined with the simethicone should be sufficient to provide a therapeutic dosage to a patient suffering from an ulcer, diarrhea, gas and associated symptoms. The effective amount of pharmaceutical combined with effective amounts of simethicone vary with the particular pharmaceutical selected. The pharmaceuticals and their preferred dosage ranges as a component of solid-dosage form containing simethicone are as follows: cimetidine with a daily dosage range from about 150 mg to about 800 mg; ranitidine with a daily dosage range of from about 50 mg to about 300 mg; famotidine with a daily dosage range of from about 5 to about 40 mg; loperamide with a daily dosage range from about 0.5 mg to about 8.0 mg; loperamide-N-oxide with a daily dosage range from about 0.25 mg to about 4.0 mg; and diphenoxylate HCl with a preferred daily dosage range from about 0.7 mg to about 10 mg. Compatible mixtures of these compounds and their pharmaceutically acceptable salts can also be included in the inventive solid dosage form.

Loperamide is the most preferred pharmaceutical for use in the present invention. Loperamide as a component of the present invention includes pharmaceutically acceptable salts of loperamide. Dosage ranges chosen for the loperamide component of the composition of the present invention depend upon the age and weight of the patient. A preferred adult dose given initially for the treatment of gastrointestinal distress is 4 mg followed by 2 mg after each unformed stool until diarrhea is controlled. A preferred ratio of simethicone to loperamide is in the range of from about 100 to 1 to about 10 to 1.

Excipient suitable for use in either bilayer include fillers, binders, sweeteners, artificial sweeteners, lubricants, glidants, disintegrants, colors, adsorbents, acidifying agents and flavoring agents. The choice of excipient will depend on the solid oral dosage form desired (i.e. tablets, pills or capsule) and whether the dosage is to be chewable or swallowed whole. The following non-limiting list of excipients illustrates excipients that could be used in a chewable solid oral dosage form:
a) an effective amount of a sweetener selected from the group consisting of mannitol, dextrose, fructose, sorbitol, sucrose and lactose;
b) an effective amount of a binder selected from the group consisting of microcrystalline cellulose, alginic acid, carboxymethyl cellulose and hydroxypropyl cellulose;
c) an effective amount of an artificial sweetener selected from the group consisting of aspartame, sucralase and saccharin;
d) an effective amount of a lubricant selected from the group consisting of magnesium stearate, talc, stearic acid, calcium stearate, zinc stearate, stearic acid, hydrogenated vegetable oil, leucine, glycerides, and sodium stearyl fumarate; and
e) an effective amount of an acidifying agent selected from the group consisting of citric acid and malic acid;
f) an effective amount of flavoring agent selected from the group consisting of artificial and natural flavors; and
g) an effective amount of a filler selected from the group consisting of dibasic calcium phosphate dihydrate and monobasic calcium phosphate monohydrate.

Other suitable excipients can be found in the *Handbook of Pharmaceutical Excipients*, published by the American Pharmaceutical Association which is incorporated herein by reference. The following formulation provides weight percentages (based on the total tablet being 100 weight percent) of the various components of a chewable multilayered tablet:

| Simethicone Layer | |
| --- | --- |
| Granulated Simethicone | 4% to 25% |
| Excipients | |
| Filler | 0% to 45% |
| Binders | 0% to 10% |
| Sweetener | 8% to 50% |
| Artificial Sweetener | 6% to 8% |
| Lubricant | 0.25% to 5.0% |
| Flavoring Agent | 0.01% to 0.03% |
| Pharmaceutical Layer | |
| Coated Granules of Antidiarrheal or antiperistaltic Excipient | 1% to 20% |
| Filler | 0% to 70% |
| Binder | 0% to 10% |
| Sweetener | 10% to 80% |
| Artificial Sweetener | 0.5% to 3% |
| Lubricant | 0.25% to 5% |
| Flavoring Agent | 0.01% to 0.03% |
| Barrier | 10% to 20% |

Suitable methods for manufacturing multilayered solid dosage forms are known in the art. Two sources for these techniques are *Remington's Pharmaceutical Science*, 18th Edition published by Mack Publishing Company and the three volume series *Pharmaceutical Dosage Forms: Tablets*, Volumes 1–3, 2nd edition, edited by Herbert A. Lieberman, Leon Lachman and Joseph B. Schwartz, published by Marcel Dekker which are hereby incorporated by reference herein.

The method for manufacturing the multilayered solid dosage form having one layer containing simethicone and one layer containing a pharmaceutical suitable for treating gastric disorders with a barrier sandwiched between the two layers comprises pressing one of two granulations each containing pharmaceutically acceptable excipients with either a therapeutic amount of simethicone or a therapeutic amount of a pharmaceutical suitable for the treatment of a gastric disorder therein, to form a first layer with one exposed surface, then coating the exposed surface with a material which is substantially impermeable to simethicone to form a coated layer with a coated surface, then contacting the coated surface with the remaining granulation, and then pressing the granulation and coated layer to form a multilayered solid oral dosage form wherein the simethicone and the pharmaceutical are separated by the material substantially impermeable to simethicone. The first layer formed in this process is generally a soft layer to allow the barrier to be put in place and provide an even appearance to the interface between the layers. The barrier may be applied as a granulation to be pressed onto a layer or spray coated on the surface of the first layer. The coatings suitable for spray coating granules of pharmaceuticals as hereinafter provided are also suitable for use as a spray on barrier layer.

In an alternate embodiment of the present invention the pharmaceutical suitable for the treatment of gastric disorders may be provided in the form of a coated granule. These granules may be formed by granulating the pharmaceutical with suitable granulation excipients in a conventional granulation process such as a wet granulation or rotogranulation.

The granules produced by these processes are preferably spherical in shape with a particle size from about 150 microns to about 500 microns for swallowable solid dosage forms and a particle range of from about 150 microns to about 300 microns for chewable (to avoid a gritty texture).

After the granulation, the granules will be coated by a conventional coating process such as roto-coating, Wurster coating or fluid bed particle coating. The coatings material for the granules of the pharmaceutical suitable for treating gastric disorders should be composed of a pharmaceutically acceptable film forming polymer which is physiologically inert, prevents the simethicone from penetrating or coating the coated granule and provides a coating that is easily broken down in the stomach (nonenteric coatings). In this embodiment the simethicone is generally free of the nonenteric coating, i.e., uncoated, so that it rapidly disperses in the stomach to provide an anti-foaming effect. Suitable coating material are nonenteric pharmaceutically acceptable film forming polymers and combinations thereof. Suitable nonenteric coatings are provided in the following Table:

| Polymer System | Coat Level | Polymer Ratio |
| --- | --- | --- |
| Cellulose Acetate/PVP | 8–18% | 90/10 to 60/40 |
| Cellulose Acetate Butyrate/PVP | 8–18% | 90/10 to 60/40 |
| Cellulose Acetate/HPC | 8–18% | 90/10 to 50/50 |
| Cellulose Acetate Butyrate/HPC | 8–18% | 90/10 to 50/50 |
| Cellulose Acetate/ Eudragit E100 | 8–18% | All ratios |
| Cellulose Acetate Butyrate/ Eudragit E 100 | 8–18% | All ratios |
| Ethyl Cellulose/PVP | 8–18% | 90/10 to 60/40 |
| Ethyl Cellulose/HPC | 8–18% | 90/10 to 50/50 |
| Ethyl Cellulose/Eudragit E 100 | 8–18% | All ratios |
| HPC | 10–20% | NA |
| HEC | 10–20% | NA |
| Eudragit E 100 | 10–20% | NA |
| HPMC | 10–20% | NA |
| HEC/HPMC | 10–20% | All ratios |
| HPC/HPMC | 10–20% | All ratios |
| HEC/HPC | 10–20% | All ratios |
| 2-vinyl pyrridine styrene co-polymer | 10–20% | NA |
| CA/2-vps | 8–18% | All ratios |
| CAB/2-vps | 8–18% | All ratios |
| Ethyl Cellulose/2-vps | 8–18% | All ratios |
| Cellulose Triacetate/PVP | 8–18% | 90/10 to 60/40 |
| Cellulose Triacetate/HPC | 8–18% | 90/10 to 50/50 |
| Cellulose Triacetate/ Eudragit E 100 | 8–18% | All ratios |

PVP — polyvinylpyrrolidone
HPC — Hydroxypropyl cellulose
HEC — Hydroxyethyl cellulose
HPMC — Hydroxypropylmethyl cellulose
CA — Cellulose Acetate
CAB — Cellulose Acetate Butyrate
2-VPS — 2-Vinyl pyridine styrene The preferred coatings are cellulose acetate, cellulose triacetate and cellulose acetate butyrate with polyvinyl pyrrolidone, methylaminoethyl-methacrylate and neutral methacrylic acid esters (Eudragit E-100), copolymers of 2-vinylpyridine and styrene and hydroxypropylcellulose. Particularly preferred grades of polymers are cellulose acetate 320-S, 398-10, 437-75S; cellulose acetate butyrate 171, 381 and 500 (both of cellulose acetate and cellulose acetate butyrate are available from FMC and fully described in *Cellulose Esters: Polymers for Drug Delivery* published in 1986); Povidone K29/32 and K90 (which is fully described in the USP); Klucel EF, LF, and JF (HPC having an average molecular weight of from about 60,000 to about 125,000); Methocel E5 and E15; Natrosol 250L; and Ethocel N10. The amount of coating applied as a weight percentage of the coated granule weight will vary with the coating process, coating granulation and granules used. The appropriate amount of coating can be determined by determining dissolution of the active pharmaceutical suitable for the treatment of gastric disorders with various coating thicknesses following the dissolution tests set forth in *The United States Pharmacopeia XXII*. As a general rule, the amount of coating will vary from about 8% to about 20% based on the weight of the coated granule. In one preferred embodiment of the present invention granules of loperamide HCl or loperamide-N-oxide formed. by a wet rotogranulation process are roto-coated with from about 8% to about 18% weight percent of a polymer blend of cellulose acetate and methylaminoethyl-methacrylate and neutral methacrylic acid ester.

A preferred granulation process for loperamide is to granulate loperamide with a granulation excipient selected from the group consisting of sugars (such as lactose, confectioners sugar or mannitol), microcrystalline cellulose, and cellulose.

The weight percentages of the components of this granulation process are as follows:

| | |
| --- | --- |
| Loperamide HCl USP | 2%–3.5% |
| Granulation Excipient | 76.5%–90% |
| Coating | 8%–20% |

In a preferred embodiment of the present invention the oral solid dosage form will contain an effective amount of simethicone and an effective amount of a pharmaceutical suitable for treating gastric disorders and at least one excipient wherein the pharmaceutical is provided in the form of coated granules which are coated with a nonenteric coating impermeable to simethicone. This dosage form may be a tablet, pill, or capsule but will preferably be provided a chewable tablet. The coating for the granules of the pharmaceutical and the excipients are the same as previously discussed above. The following formulation provides weight percentage ranges (based on the total weight percent equalling 100 weight percent) of the various components of a chewable tablet.

| | |
| --- | --- |
| Granulated Simethicone | 4% to 35% |
| Coated Granules of Loperamide | 2% to 8% |
| Excipients | |
| Filler | 0% to 55% |
| Binders | 0% to 20% |
| Sweetener | 0% to 75% |
| Artificial Sweetener | 0% to 10% |
| Lubricant | 0.25% to 6.0% |
| Flavoring Agent | 0.25% to 2.0% |

Suitable methods for making solid dosage forms are well known in the art such as are described in *Pharmaceutical Dosage Forms: Tablets*, by Lieberman et al. One suitable method is to wet granulate the components and compress to a tablet on a rotary tablet press.

In a further embodiment of the present invention the coated granules of the pharmaceutical can be used in the multilayered solid dosage form previously described.

The following examples are provided to further illustrate the present invention.

EXAMPLE I

This Example provides a comparison of the dissolution profile of loperamide when admixed in a solid oral dosage form with simethicone as compared to the dissolution profile of loperamide added in a separate solid dosage form from simethicone. The solid oral dosage forms for loperamide and simethicone added separately were commercially available chewable tablets sold as Imodium® and Mylicon® which provided equivalent dosages of loperamide and simethicone. The dissolution of loperamide was tested using the protocol set forth in the *United States Pharmacopeia*, (1990) as modified by Supplement 1. The results of these tests were then plotted as percent by weight of the claimed amount of loperamide recovered vs. time.

The first experimental solid oral dosage form containing loperamide and simethicone was formed using the following ingredients:

| Ingredient | Mg/Tablets |
| --- | --- |
| Simethicone GS-J | 328.0 |
| Loperamide HCl, USP | 2.0 |
| Dibasic Calcium Phosphate filler | 875.1 |
| Sodium Starch Glycolate | 114.6 |
| Colloidal Silicon Dioxide, NF | 57.3 |
| Croscarmellose Sodium, NF | 57.3 |
| Totals | 1434.3 |

The first experimental tablet was manufactured in the following manner:
1. Blend loperamide HCl and 6.1 g of dibasic calcium phosphate in a planetary mixer (Hobart mixer).
2. Add the simethicone, colloidal silicon dioxide and the remaining dibasic calcium phosphate to the planetary mixer (speed 1) and mix for two (2) minutes.
3. Add the loperamide HCl/dibasic calcium phosphate blend to the planetary mixer and mix for one (1) minute.
4. Add the disintegrants (sodium starch glycolate, croscarmellose sodium) to the planetary mixer and mix for an additional three (3) minutes.
5. Compress blend on a Stokes press using a single punch. The blend could be passed through a 24 mesh screen to try to break-up small aggregates of colloidal silicon dioxide.

A second experimental tablet was formed from the following ingredients:

| Ingredient | Mg/Tablets |
| --- | --- |
| Simethicone GS-J | 328.0 |
| Loperamide HCl, USP | 2.0 |
| Dibasic Calcium Phosphate, USP | 875.1 |
| Sodium Starch Glycolate, NF | 114.6 |
| Colloidal Silicon Dioxide, NF | 57.3 |
| Croscarmellose Sodium, NF | 57.3 |
| Total | 1434.3 |

DIRECTIONS:
Follow the manufacturing directions for the first experimental tablet as set forth above except:
1. In Step 2, screen the colloidal silicon dioxide with some of the dibasic calcium phosphate (through a 25 mesh screen).
2. Then compress as described in Step 5.

A third experimental tablet was formed with the following ingredients:

| Ingredient | Mg/Tablet |
| --- | --- |
| Simethicone, USP | 125.0 |
| Dibasic Calcium Phosphate, USP | 370.0 |
| Microcrystalline Cellulose, NF | 265.5 |
| Colloidal Silicon Dioxide, NF | 31.5 |
| Sodium Starch Glycolate, NF | 72.0 |
| Croscarmellose Sodium, NF | 36.0 |
| Loperamide HCl, USP | 2.0 |
| Total | 902.0 |

DIRECTIONS:
The third experimental tablet was manufactured in the following manner:
1. Mix loperamide HCl, dibasic calcium phosphate and microcrystalline cellulose in a planetary mixer (Hobart mixer) for 30 seconds.
2. Granulate by adding simethicone into Step 1 for 1 minute.
3. While mixing add colloidal silicon dioxide to Step 2 for 2.5 minutes.
4. Add sodium starch glycolate and croscarmellose sodium and mix for 1 minute.
5. Compress the tablets as set forth above for the first experimental tablet.

Figure 6:
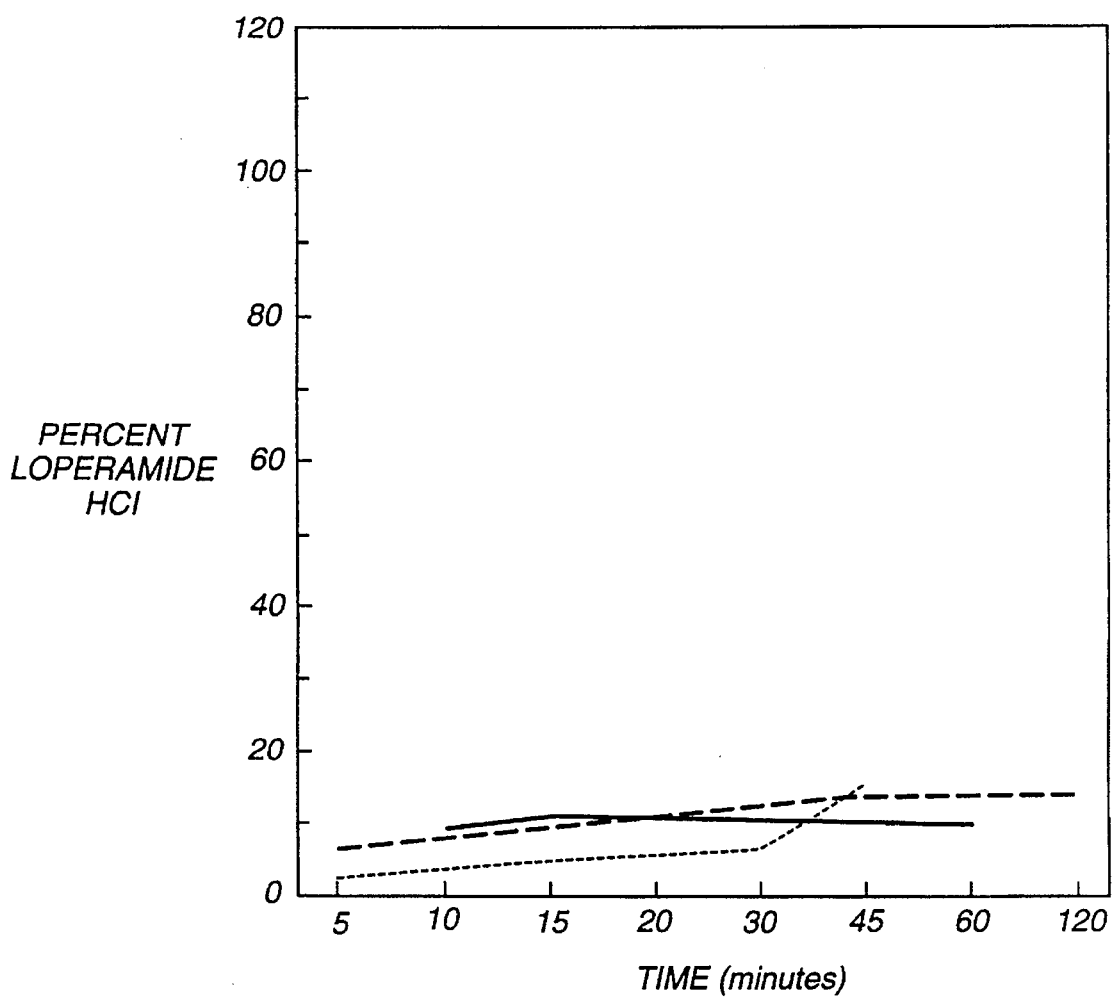
FIG. 6 provides dissolution profiles for three formulations of uncoated loperamide present with simethicone provided in an admixed single solid oral dosage form. The solid line indicates the dissolution profile of loperamide from a solid dosage form comprised of Simethicone GS-J (40% simethicone adsorbed onto a diluent) and uncoated granules containing loperamide. The dashed line indicates the dissolution profile of loperamide from a second solid dosage form containing granules of Simethicone GS-J (40% simethicone adsorbed onto a diluent) and uncoated granules containing loperamide. The dotted line indicates the dissolution profile of loperamide from a third solid dosage form containing granules of Simethicone GS-J (40% simethicone adsorbed onto a diluent) and uncoated granules containing loperamide. The formulations for these solid dosage forms are contained in Example I.

FIG. 5 shows the dissolution profile of simethicone and loperamide when provided in separate solid oral dosage form. As is shown in FIG. 6, the dissolution profile of loperamide in tablets containing both loperamide and simethicone in a single solid oral dosage form was reduced to the point that almost no loperamide was detected. The solid, dashed and dotted lines in FIG. 6 represent the dissolution profiles for the first, second and third experimental tablets, respectively. These results demonstrate the need for a new solid oral dosage form containing a combination of simethicone and a pharmaceutical suitable for the treatment of a gastric disorders.

EXAMPLE II

This Example provides a formulation for making a tablet that contains coated loperamide granules admixed with granules of simethicone and formed into a solid oral dosage form. The weight provided hereinafter are based on a unit tablet weight for a 1290 mg tablet The coated granules of loperamide were prepared by a rotary wet granulation process employing 2.0 mg. of loperamide HCl USP, 52 mg of confectioners sugar NF, 5.8 mg of microcrystalline cellulose and purified water USP. The granules produced by the wet granulation were then rotocoated with a mixture of 4.57 mg of cellulose acetate (FMC 389-10) and 6.86 mg of methylaminoethylmethacrylate and neutral methacrylic acid ester (sold commercially under the name Eudragit E-100) provided in a solution of 82.30 mg of acetone and 20.58 mg of methanol.

The tablets were made using the following ingredients:

| Simethicone Blend | |
| --- | --- |
| Simethicone (GS-J, Granular, Union Carbide) | 328.0 mg |
| Sorbitol NF (Instant Pharma) | 328.0 mg |
| Loperamide Blend | |
| Loperamide HCl (Rotogranulated/ coated: to deliver 2 mg of active) | 71.4 mg |

-continued

| | |
|---|---|
| Dextrates NF | 466.9 mg |
| Vanilla Mint Flavor | 9.8 mg |
| Aspartame NF | 15.0 mg |
| D&C Yellow No. 10 Al. Lake (17% Certified) | 0.04 mg |
| FD&C Blue No. 1 Al. Lake (31% Certified) | 0.01 mg |
| Lubricant Blend | |
| Stearic Acid NF | 6.4 mg |
| Tribasic Calcium Phosphate NF | 64.5 mg |
| Tablet weight | 1290 mg |

MANUFACTURING DIRECTIONS

Simethicone Blend

1. Place simethicone and sorbitol in a 16 quart P-K Twin Shell Blender. Blend for 2 minutes.

Loperamide Blend

1. Screen D&C Yellow No. 10 Al. Lake and FD&C Blue No. 1 Al. Lake through 60 mesh screen.
2. Add rotogranulated/coated loperamide HCl, dextrates, vanilla mint flavor, aspartame NF, D&C Yellow No. 10 Al. Lake, and FD&C Blue No. 1 Al. Lake to the P-K Blender. Blend for 5 minutes.

Lubricant Blend

1. Screen stearic acid through a 60 mesh screen.
2. Add stearic acid and tribasic calcium phosphate NF to the P-K Blender. Blend for 3 minutes.

Discharge contents of blender in a properly sized and labelled bag. Screen through a 12 mesh screen, if necessary. Reconcile blending yield.

Tablet Compression

1. Compress the blend into tablets to the following specifications on a Beta press rotary tablet machine equipped with the specified tooling:

Punches: ⅝ inch×0.018 inch, 0.002 inch blended land, flat faced beveled edge

Dies: ⅝ inch round

Group Weight (10 tablets): Target −12.9 grams (Range: 12.64–13.16 grams)

Thickness: Target 5.0 mm (Range 4.9 to 5.15)

Hardness: Target 4.0 kp (Range 2.9 to 4.9)

Friability (%): 100 drops NMT (not more than) 5.0%

Defoam Time: LT (less than) 45 seconds

2. Collect compressed tablets into a properly labelled container.

Figure 7:
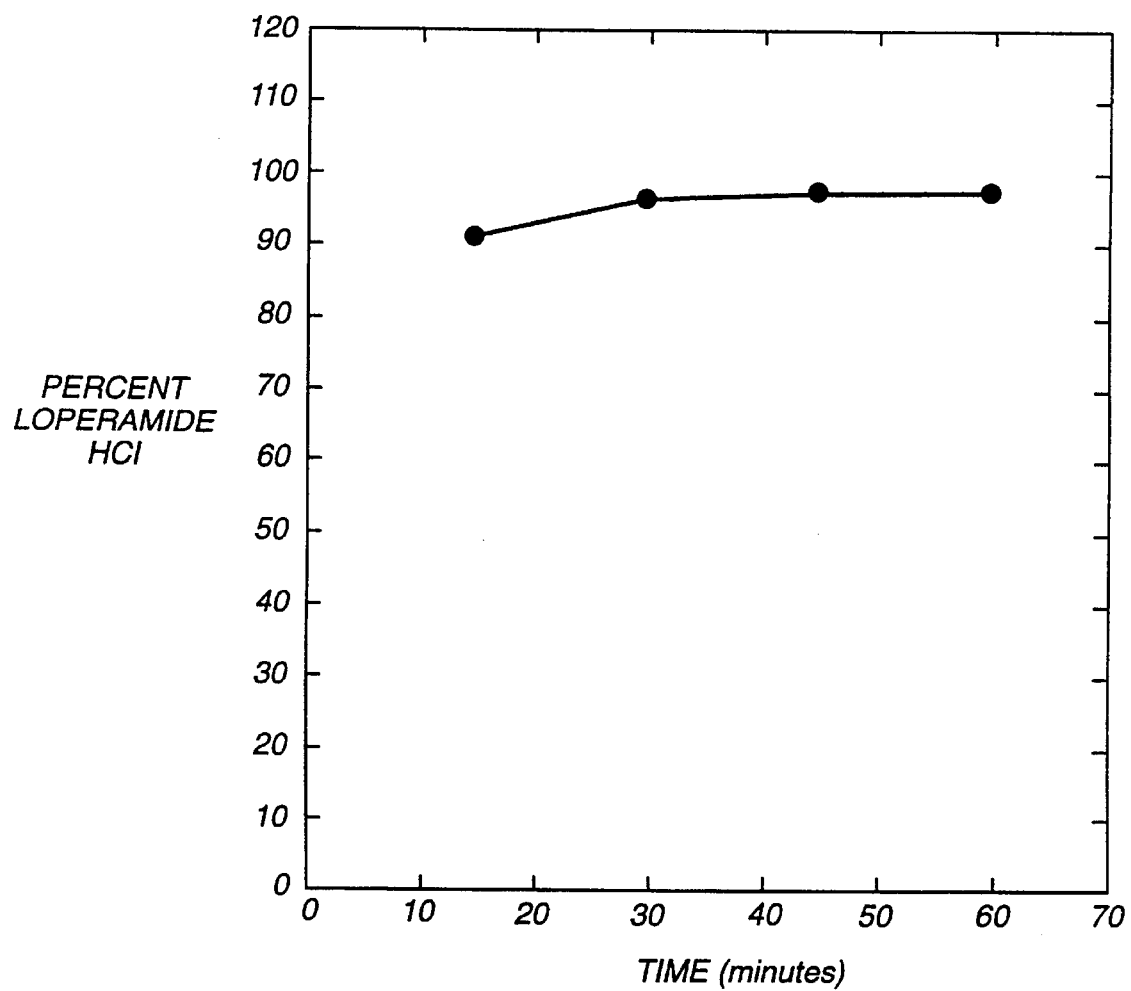
FIG. 7 provides a dissolution profile for a tablet that contains coated loperamide HCl granules admixed with granules of simethicone. The formulation for this tablet is contained in Example II.

The dissolution profile, determined by the procedure set forth in Example I, is shown in FIG. 7. The dissolution rate for the tablet containing coated loperamide granules improved substantially over the rate shown in FIG. 6 for the tablet containing uncoated loperamide granules.

EXAMPLE III

This Example provides a formulation for making a tablet that contains coated loperamide granules admixed with a simethicone granulating liquid and formed into a solid oral dosage form. The simethicone granulating liquids were prepared with water or water/propanol, and are designated as aqueous and solvent wet granulation, respectively.

The granules of loperamide were prepared by the rotary process described in Example II.

The tablets were made using the following ingredients:

| | Wet Granulation | |
|---|---|---|
| | Aqueous (mg/tab) | Solvent (mg/tab) |
| A. Simethicone | | |
| Simethicone, USP | 125.0 | 125.0 |
| Sterile Water, USP | 87.5[1] | 62.0[1] |
| 2-Propanol, USP (anhydrous) | — | 25.5[1] |
| Povidone, USP | 25.0 | 25.0 |
| B. Loperamide | | |
| Loperamide, HCl, USP (Rotogranulated/coated: to deliver 2 mg of active) | 72.0 | 72.0 |
| Mannitol, USP | 540.0 | 540.0 |
| Lactose, NF (Fast-Flo) | 538.2 | 538.2 |
| Microcrystalline Cellulose, NF (PH-101) | 30.0 | 30.0 |
| Total Tablet Weight | 1330.2 | 1330.2 |

[1]volatilized in processing

MANUFACTURING DIRECTIONS

Aqueous Wet Granulation:

1. Prepare simethicone granulation liquid by mixing sterile water, povidone, and simethicone in a stainless steel container with a mixer.
2. Blend mannitol, microcrystalline cellulose, rotogranulated/coated loperamide and lactose in a planetary mixer (Hobart mixer) for 3.5 minutes.
3. Granulate by adding granulation liquid from Step 1 into the Hobart mixer. Mix it for 7.5 minutes.
4. Screen the simethicone loperamide granulation through a 10 mesh screen.
5. Dry-the granulation in an oven for one hour and forty-five minutes at 60° C.
6. Compress the tablets on a tablet press.

Solvent Wet Granulation:

Follow directions for manufacturing the Aqueous Wet Granulation set forth above, except:

1. Prepare simethicone granulation liquid by mixing sterile water, 2-propanol (anhydrous), povidone, and simethicone in a stainless steel container with an appropriate mixer.

The dissolution profiles determined by the procedure set forth in Example I are shown in FIG. 8. The solid and dashed lines represent the dissolution profiles for the aqueous and solvent granulated tablets, respectively. The dissolution rates for the aqueous and solvent granulated tablets containing coated loperamide granules improved stability over the rate shown in FIG. 6 for the tablet containing uncoated loperamide granules.

Reasonable variations can be made in view of the disclosure above without departing from the spirit and scope of this invention.

What is claimed is:

1. A method for manufacturing a multilayered solid dosage form having one layer containing simethicone and one layer containing a pharmaceutical for treating gastric disorders selected from the group consisting of cimetidine, ranitidine, famotidine, diphenoxylate, loperamide, loperamide-N-oxide, pharmaceutically acceptable salts thereof and combinations thereof with a barrier sandwiched between the two layers comprising pressing one of two granulations each containing pharmaceutically acceptable excipients with either a therapeutic amount of simethicone or a therapeutic amount of said pharmaceutical for the treatment of a gastric disorder therein, to form a first layer with one exposed surface; forming said barrier by coating the exposed surface with a pharmaceutically acceptable polymer which is substantially impermeable to simethicone to form a coated layer with coated surface; contacting the coated surface with the remaining granulation; and pressing the granulation and coated layer to form a multilayered solid oral dosage form wherein the simethicone and the pharmaceutical are separated by the polymer substantially impermeable to simethicone.

2. The method of claim 1 wherein the pharmaceutical comprises loperamide HCl.

3. The method of claim 1 wherein the pharmaceutical comprises diphenoxylate.

4. The method of claim 1 wherein the pharmaceutical comprises famotidine.

5. The method of claim 1 wherein the pharmaceutical comprises loperamide-N-oxide.

* * * * *